United States Patent
Lin et al.

(10) Patent No.: US 7,381,386 B2
(45) Date of Patent: *Jun. 3, 2008

(54) EXTRACTION PROCESS FOR REMOVAL OF IMPURITIES FROM MOTHER LIQUOR IN THE SYNTHESIS OF CARBOXYLIC ACID

(75) Inventors: Robert Lin, Kingsport, TN (US); Marcel de Vreede, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 534 days.

This patent is subject to a terminal disclaimer.

(21) Appl. No.: 10/455,018

(22) Filed: Jun. 5, 2003

(65) Prior Publication Data

US 2004/0249208 A1    Dec. 9, 2004

(51) Int. Cl.
*C07C 51/00*    (2006.01)

(52) U.S. Cl. .................. 423/49; 562/414; 562/416; 562/485; 562/486; 562/487

(58) Field of Classification Search ............. 423/49; 562/414, 485, 416, 486, 487
See application file for complete search history.

(56) References Cited

U.S. PATENT DOCUMENTS

| | | | |
|---|---|---|---|
| 2,964,559 A | 12/1960 | Burney et al. | |
| 3,840,641 A | 10/1974 | Wampfler et al. | |
| 3,873,468 A | 3/1975 | Kobinata et al. | |
| 3,950,409 A | 4/1976 | Yokota et al. | |
| 3,996,271 A | 12/1976 | Yokota et al. | |
| 4,081,464 A | 3/1978 | Marsh et al. | |
| 4,158,738 A | 6/1979 | Scott et al. | |
| 4,185,073 A | 1/1980 | Marsh et al. | |
| 4,219,669 A | 8/1980 | Tsuchiya et al. | |
| 4,298,580 A | 11/1981 | Harper et al. | |
| 4,330,676 A | 5/1982 | Moxham | |
| 4,356,319 A | 10/1982 | Roffia et al. | |
| 4,769,489 A | 9/1988 | Abrams et al. | |
| 4,914,230 A | 4/1990 | Abrams et al. | |
| 4,939,297 A | 7/1990 | Browder et al. | |
| 5,200,557 A | 4/1993 | Gee et al. | |
| 5,643,468 A | 7/1997 | Ure | |
| 5,676,847 A | 10/1997 | Yamamoto et al. | |
| 5,705,682 A * | 1/1998 | Ohkoshi et al. ............ | 562/414 |
| 5,770,765 A | 6/1998 | Ohkashi | |
| 5,840,965 A | 11/1998 | Turner et al. | |
| 5,916,422 A | 6/1999 | Kimura et al. | |
| 5,955,394 A | 9/1999 | Kelly | |
| 6,054,610 A | 4/2000 | Lee et al. | |
| 6,153,790 A | 11/2000 | June et al. | |
| 7,074,954 B2 | 7/2006 | Sheppard et al. | |
| 7,132,566 B2 | 11/2006 | Sumner et al. | |
| 2002/0016500 A1 | 2/2002 | Matsumoto et al. | |
| 2002/0193630 A1 | 12/2002 | Lin et al. | |
| 2004/0245176 A1 | 12/2004 | Parker et al. | |

FOREIGN PATENT DOCUMENTS

| | | |
|---|---|---|
| DE | 2131470 A | 6/1970 |
| EP | 0 181 127 A2 | 5/1986 |
| EP | 0 764 627 A1 | 3/1997 |
| EP | 0579715 B1 | 8/1997 |
| EP | 1 484 305 A1 | 8/2004 |
| EP | 1 484 306 A1 | 8/2004 |
| GB | 892766 | 3/1962 |
| GB | 1407705 | 9/1975 |
| GB | 2067563 | 7/1981 |
| JP | 46-14339 B | 4/1971 |
| JP | 49-123191 A | 11/1974 |
| JP | 51-145488 A | 12/1976 |
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |

(Continued)

OTHER PUBLICATIONS

U.S. Appl. No. 10/455,016, filed Jun. 5, 2003, Lin.

(Continued)

*Primary Examiner*—Steven Bos
(74) *Attorney, Agent, or Firm*—Steven A. Owen; Bernard J. Graves, Jr.

(57) ABSTRACT

A method for removing impurities from a mother liquor comprising a carboxylic acid, a metal catalyst, impurities by (a) evaporating the mother liquor comprising a carboxylic acid, a metal catalyst, impurities and a solvent in a first evaporator zone to produce a vapor stream and a concentrated mother liquor stream; (b) evaporating the concentrated mother liquor stream in a second evaporator zone to form a solvent rich stream and a super concentrated mother liquor stream; (c) mixing in a mixing zone a water-solvent solution and optionally an extraction solvent with the super concentrated mother liquor stream to form an aqueous mixture; (d) optionally separating organic impurities from the aqueous mixture in a solid-liquid separation zone to form a purified aqueous mixture; and (e) extracting the aqueous mixture or purified aqueous mixture with an extraction solvent in an extraction zone to form an extract stream and the raffinate stream.

17 Claims, 1 Drawing Sheet

FOREIGN PATENT DOCUMENTS

| | | |
|---|---|---|
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | WO 92/18453 | 10/1992 |
| WO | WO 92/18454 A1 | 10/1992 |
| WO | WO 93/24441 A | 12/1993 |
| WO | WO 97/27168 A1 | 7/1997 |
| WO | WO 97/30963 A | 8/1997 |
| WO | WO 00/31014 A1 | 6/2000 |
| WO | WO 01/55075 A2 | 8/2001 |

OTHER PUBLICATIONS

U.S. Appl. No. 10/455,017, filed Jun. 5, 2003, Lin et al.
BHS—Werk Sonthofen, *BHS-FEST Pressure Filter*, 1990, pamphlet, Santhofen, West Germany.
Copending U.S. Appl. No. 10/948,591, filed Sep. 24, 2004.
Copending U.S. Appl. No. 10/948,678, filed Sep. 24, 2004.
Copending U.S. Appl. No. 10/975,256, filed Oct. 28, 2004.
Copending U.S. Appl. No. 10/975,252, filed Oct. 28, 2004.
Office Action for copending U.S. Appl. No. 10/455,017.
USPTO office action dated Jul. 19, 2006 for copending U.S. Appl. No. 10/455,017.
USPTO office action dated Jul. 19, 2006 for copending U.S. Appl. No. 10/455,016.
Treybal, Robert E., "Stagewise Contact, Single-Stage Extraction," Mass-Transfer Operations, Third Edition, 1980, pp. 490-555, McGraw-Hill Book Company.
USPTO Office Action dated Mar. 14, 2007, for copending U.S. Appl. No. 10/455,016.
USPTO office action dated Jan. 18, 2007 for copending U.S. Appl. No. 10/455,017.
Copending U.S. Appl. No. 11/655,395, filed Jan. 19, 2007, Philip E. Gibson et al.
Copending U.S. Appl. No. 11/655,317, filed Jan. 19, 2007, Philip E. Gibson et al.
Copending U.S. Appl. No. 11/655,396, filed Jan. 19, 2007, Kenny R. Parker et al.
USPTO office action dated Nov. 30, 2006 for copending U.S. Appl. No. 10/975,256.
USPTO office action dated Nov. 30, 2006 for copending U.S. Appl. No. 10/975,252.
Copending U.S. Appl. No. 11/839,575, filed Aug. 16, 2007, Philip Edward Gibson et al.
Copending U.S. Appl. No. 11/839,578, filed Aug. 16, 2007, Philip Edward Gibson et al.
Copending U.S. Appl. No. 11/839,582, filed Aug. 16, 2007, Philip Edward Gibson et al.
Copending U.S. Appl. No. 11/839,573, filed Aug. 16, 2007, Kenny Randolph Parker et al.
Notice of Allowance dated Aug. 1, 2007 for copending U.S. Appl. No. 10/975,252.
Notice of Allowance dated Jul. 18, 2007 for copending U.S. Appl. No. 10/975,256.
USPTO Office Action dated Jul. 6, 2007 for copending U.S. Appl. No. 10/455,016.
USPTO Office Action dated May 17, 2007 for copending U.S. Appl. No. 11/201,512.
USPTO Office Action dated May 11, 2007 for copending U.S. Appl. No. 10/455,017.
Copending U.S. Appl. No. 11/842,413, filed Aug. 21, 2007, Kenny Randolph Parker et al.
USPTO Office Action dated Sep. 11, 2007 for copending U.S. Appl. No. 10/455,017.

* cited by examiner

EXTRACTION PROCESS FOR REMOVAL OF IMPURITIES FROM MOTHER LIQUOR IN THE SYNTHESIS OF CARBOXYLIC ACID

FIELD OF INVENTION

This invention relates to the recovery of a metal catalyst from a mother liquor produced in the synthesis of carboxylic acid, typically terephthalic acid. More particularly, the process involves the addition of water to a super concentrated mother liquor stream to recover the metal catalyst and then subjecting an aqueous mixture or purified aqueous mixture so formed to a single stage extraction to remove organic impurities to produce an extract stream and a raffinate stream comprising the metal catalyst.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities present due to the oxidation of paraxylene.

Terephthalic acid (TPA) is an intermediate in the production of polyesters for plastics and fiber applications. Commercial processes for the manufacture of TPA are based on the heavy-metal catalyzed oxidation of p-xylene, generally with a bromide promoter in acetic acid solvent. Due to the limited solubility of TPA in acetic acid under practical oxidation conditions, a slurry of TPA crystals is formed in the oxidation reactor. Typically, the TPA crystals are withdrawn from the reactor and separated from the reaction mother liquor using conventional solid-liquid separation techniques. The mother liquor, which contains most of the catalyst and promoter used in the process, is recycled to the oxidation reactor. Aside from the catalyst and promoter, the mother liquor also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions in the oxidation of p-xylene to terephthalic acid. The solid TPA crystals obtained by solid-liquid separation are generally washed with fresh solvent to displace the major portion of the mother liquor and then dried to remove most of the acetic acid solvent. The dried, crude TPA crystals are contaminated with impurities that were present in the mother liquor since these impurities are co-precipitated with the TPA crystals. Impurities are also present due to occlusion in the TPA crystal structure and due to incomplete removal of the mother liquor by the fresh solvent wash.

Many of the impurities in the mother liquor that are recycled are relatively inert to further oxidation. Such impurities include, for example, isophthalic acid, phthalic acid and trimellitic acid. Impurities, which undergo further oxidation are also present, such as, for example, 4-carboxybenzaldehyde, p-toluic acid and p-tolualdehyde. The concentration of oxidation inert impurities tends to accumulate in the mother liquor. The concentration of these inert impurities will increase in the mother liquor until an equilibrium is reached whereby the amount of each impurity contained in the dry TPA product balances its rate of formation or addition to the oxidation process. The normal level of impurities in crude TPA makes it unsuitable for direct use in most polymer applications.

Traditionally, crude TPA has been purified either by conversion to the corresponding dimethyl ester or by dissolution in water with subsequent hydrogenation over standard hydrogenation catalysts. More recently, secondary oxidative treatments have been used to produce polymer-grade TPA. Irrespective of the method used to purify TPA to render it suitable for use in polyester manufacture, it is desirable to minimize the concentrations of impurities in the mother liquor and thereby facilitate subsequent purification of TPA. In many cases, it is not possible to produce a purified, polymer-grade TPA unless some means for removing impurities from the mother liquor is utilized.

One technique for impurity removal from a recycle stream commonly used in the chemical processing industry is to draw out or "purge" some portion of the recycle stream. Typically, the purge stream is simply disposed of or, if economically justified, subjected to various treatments to remove undesired impurities while recovering valuable components. One example is U.S. Pat. No. 4,939,297 herein incorporated by reference. The amount of purge required for control of impurities is process-dependent; however, a purge amount equal to 10-40% of the total mother liquor is usually sufficient for TPA manufacture. In the production of TPA, the level of mother liquor purge necessary to maintain acceptable impurity concentrations, coupled with the high economic value of the metal catalyst and solvent components of the mother liquor, make simple disposal of the purge stream economically unattractive. Thus, there is a need for a process that recovers essentially all of the expensive metal catalysts and acetic acid contained in the mother liquor while removing a major portion of the impurities present in the purge stream. The metal catalyst should be recovered in an active form suitable for reuse by recycling to the p-xylene oxidation step.

This invention is a marked improvement over a typical purge process. Some of the advantages are:
 1) enhanced operability and reliability due to reduction in plugging potential; and
 2) reduction in overall energy usage.

The invention enhances the impurity removal efficacy of the process, and the operability of the process compared to the existing processes.

SUMMARY OF THE INVENTION

This invention relates to removal of impurities and the recovery of a metal catalyst from mother liquor produced in the synthesis of carboxylic acid, typically terephthalic acid. More particularly, the process involves the addition of water to a concentrated mother liquor to recover the metal catalyst and then subjecting an aqueous mixture so formed to a single stage extraction to remove organic impurities to produce an extract stream and a raffinate stream.

It is an object of this invention to provide a process to produce a super concentrated mother liquor stream.

It is yet another object of this invention to provide a process to recover a metal catalyst from a mother liquor stream.

It is yet another object of this invention to provide a process for removal of impurities and the recovery of a metal catalyst from mother liquor produced in the synthesis of carboxylic acid.

In a first embodiment of this invention, a process to recover a metal catalyst from a mother liquor is provided. The process comprises the following steps:
 (a) evaporating a mother liquor comprising a carboxylic acid, the metal catalyst, impurities, water and a solvent in a first evaporator zone to produce a vapor stream and a concentrated mother liquor stream;

(b) evaporating the concentrated mother liquor stream in a second evaporator zone to form a solvent rich stream and a super concentrated mother liquor stream;

(c) mixing in a mixing zone a water-solvent solution with the super concentrated mother liquor stream to form an aqueous mixture;

(d) optionally separating organic impurities from the aqueous mixture in a solid-liquid separation zone to form a purified aqueous mixture;

(e) adding an extraction solvent to the aqueous mixture or the purified aqueous mixture in an extraction zone to form an extract stream and a raffinate stream; and (f) optionally separating the extract stream and the solvent rich stream in a separation zone to form a high boiling point organic impurities stream and a recovered extraction solvent stream.

In another embodiment of this invention, a process to produce a super concentrated mother liquor stream is provided. The process comprises the following steps:

(a) evaporating a mother liquor comprising a carboxylic acid, a metal catalyst, impurities, water and a solvent in a first evaporator zone to produce a vapor stream and a concentrated mother liquor stream; and (b) evaporating the concentrated mother liquor stream in a second evaporator zone to produce a solvent rich stream and a super concentrated mother liquor stream wherein the evaporating in step (a) and step b) combined removes about 95 wt % to about 99 wt % of the water and solvent from the mother liquor.

In another embodiment of this invention, a process to recover a metal catalyst from a mother liquor is provided. The process comprises the following steps:

(a) evaporating a mother liquor comprising a carboxylic acid, the metal catalyst, impurities, water and a solvent in a first evaporator zone to produce a vapor stream and a concentrated mother liquor stream;

(b) evaporating the concentrated mother liquor stream in a second evaporator zone to form a solvent rich stream and a super concentrated mother liquor stream;

(c) mixing in a mixing zone a water-solvent solution and optionally an extraction solvent with the super concentrated mother liquor stream to form an aqueous mixture;

(d) adding an extraction solvent to the aqueous mixture in an extraction zone to form an extract stream and the raffinate stream; and (e) optionally separating the extract stream and the solvent rich stream in a separation zone to form a high boiling point organic impurities stream and a recovered extraction solvent stream.

In another embodiment of the invention, a process to recover a metal catalyst from a mother liquor is provided. The process comprises the following steps:

(a) evaporating the mother liquor in a first evaporator zone to produce a vapor stream and a concentrated mother liquor stream wherein about 50 wt % to about 80 wt % of the solvent and water is removed from the mother liquor;

(b) evaporating the concentrated mother liquor stream in a second evaporator zone to form a solvent-rich stream and a super concentrated mother liquor stream wherein about 95 wt % to about 99 wt % of solvent and water are removed from the mother liquor in the combined step (a) and step (b);

(c) mixing a water-solvent solution with the super concentrated mother liquor stream to form an aqueous mixture; wherein the water-solvent solution is added to quench the aqueous mixture to a temperature range of about 60° C. to about 95° C.;

(d) optionally separating organic impurities from the aqueous mixture in a solid-liquid separation zone to form a purified aqueous mixture;

(e) extracting the aqueous mixture or the purified aqueous mixture with an extraction solvent in an extraction zone to form an extract stream and a raffinate stream wherein the extraction zone comprises a single stage extractor; and (f) separating the extract stream and the solvent rich stream in a separation zone to form a high boiling point organic impurities stream and a recovered extraction solvent stream.

In another embodiment of the invention, a process to recover a metal catalyst from a mother liquor is provided. The process comprises the following steps:

(a) evaporating the mother liquor in a first evaporator zone to produce a vapor stream and a concentrated mother liquor stream wherein about 50 wt % to about 80 wt % of the solvent and water is removed from the mother liquor;

(b) evaporating the concentrated mother liquor stream in a second evaporator zone to form a solvent-rich stream and a super concentrated mother liquor stream wherein about 95 wt % to about 99 wt % of solvent and water are removed from the mother liquor in the combined step (a) and step (b);

(c) mixing in a mixing zone a water-solvent solution and optionally an extraction solvent with the super concentrated mother liquor stream to form an aqueous mixture; wherein the water-solvent solution is added to quench the aqueous mixture to a temperature range of about 60° C. to about 95° C.;

(d) extracting the aqueous mixture or the purified aqueous mixture with an extraction solvent in an extraction zone to form an extract stream and a raffinate stream wherein the extraction zone comprises a single stage extractor; and (e) separating the solvent organic impurities stream and the solvent rich stream in a separation zone to form a high boiling point organic impurities stream and a recovered extraction solvent stream.

In another embodiment of this invention, a composition is provided. The composition comprises acetic acid, water, isophthalic acid, benzoic acid, 4-carboxybenzaldehyde, terephthalic acid, and cobalt; wherein the sum aggregrate of the isophthalic acid, benzoic acid, 4-carboxybenzaldehyde, and terephthalic acid comprise between about 5 wt % to 80% of the concentrated mother liquor. These objects, and other objects, will become more apparent to others with ordinary skill in the art after reading this disclosure.

DESCRIPTION OF THE INVENTION

Figure 1:
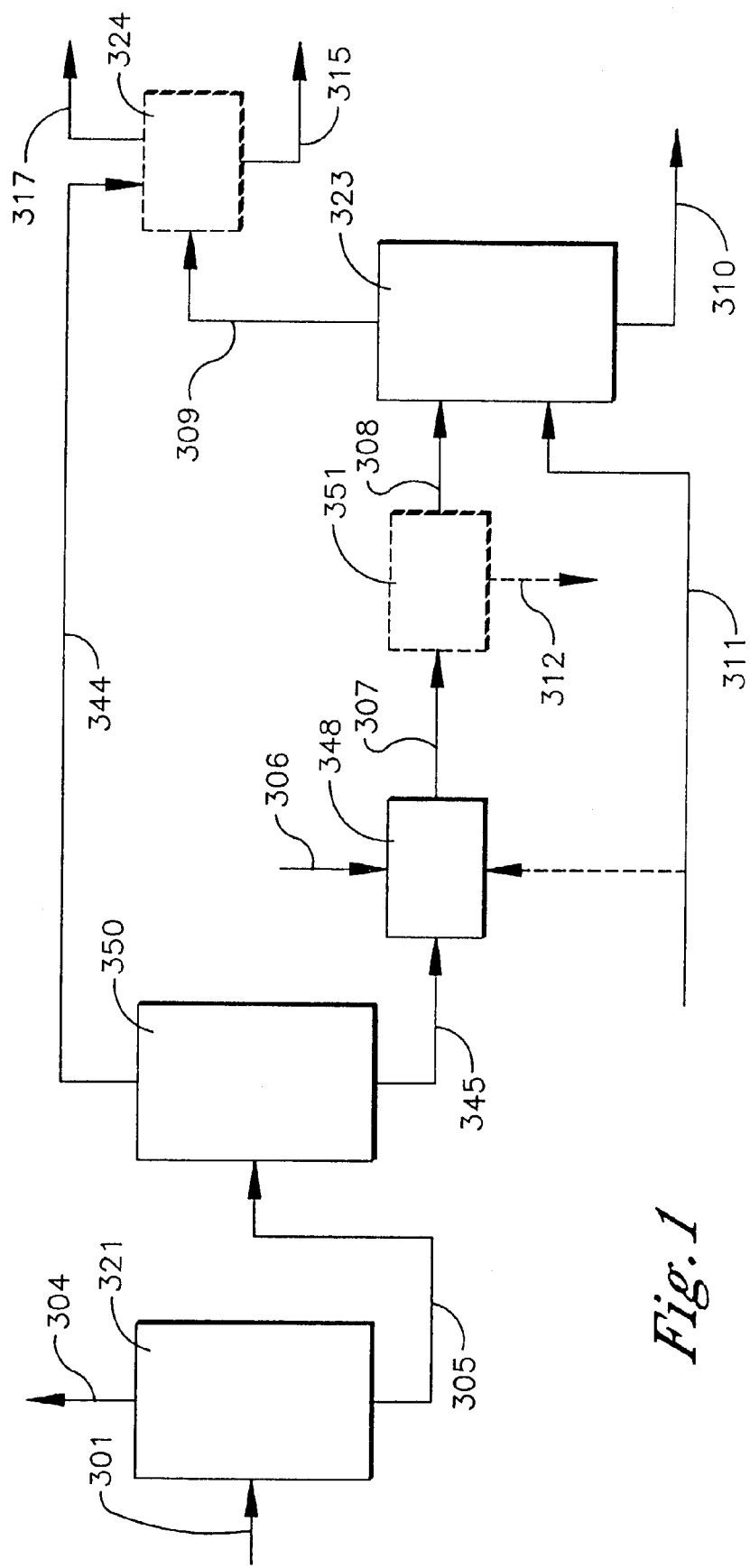
FIG. 1 illustrates different embodiments of the invention where a process to recover a metal catalyst from a mother liquor and a process to produce a super concentrated mother liquor stream are provided.

In one embodiment of this invention, a process to recover a metal catalyst from a mother liquor 301 is provided as shown in FIG. 1. The process comprises the following steps.

Step (a) comprises evaporating a mother liquor 301 comprising a carboxylic acid, the metal catalyst, impurities, water and a solvent in a first evaporator zone 321 to produce a vapor stream 304 and a concentrated mother liquor stream 305.

The mother liquor 301 is withdrawn from a carboxylic acid oxidative synthesis process. The mother liquor 301 serves as the feed stream to the present process. The mother liquor comprises carboxylic acid, water, a solvent, the metal catalyst and impurities. The impurities comprise organic bromides and corrosion metals. The organic bromides are used as promoters in the oxidation reaction. Examples of corrosion metals are iron and chromium compounds, which inhibit, reduce or entirely destroy the activity of the metal catalyst.

Suitable carboxylic acids are selected from the group consisting of terephthalic acid, isophthalic acid, naphthalene dicarboxylic acid, and mixtures thereof.

Suitable solvents include aliphatic mono-carboxylic acids, preferably containing 2 to 6 carbon atoms, or benzoic acid and mixtures thereof and mixtures with water. Preferably, the solvent is acetic acid mixed with water, in a ratio of about 5:1 to about 25:1, preferably between about 10:1 and about 15:1. Throughout the specification, acetic acid will be referred to as the solvent. However, it should be appreciated that other suitable solvents, such as those disclosed here, may also be utilized.

In the first step of the present process, the mother liquor is concentrated by conventional means in a first evaporator zone 321 comprising an evaporator to produce a vapor stream 304 and a concentrated mother liquor stream 305. The evaporator is operated at atmospheric or slightly superatmospheric conditions, generally from about 1 atmosphere to about 10 atmospheres. The vapor stream 304 comprises a majority of the water and solvent, and the concentrated mother liquor stream 305 comprises the remainder of the water and solvent not removed from the mother liquor. The evaporation removes about 50 wt % to about 80 wt % of the solvent and water, typically acetic acid and water, which are present in the mother liquor.

Step (b) comprises evaporating the concentrated mother liquor stream 305 in a second evaporator zone 350 to produce a solvent rich stream 344 and a super concentrated mother liquor stream 345.

The concentrated mother liquor stream 305 is then introduced in the second evaporator zone 350, which comprises at least one evaporator. The evaporator is operated at super atmospheric or pressurized conditions, generally from about 1 atmosphere to about 10 atmospheres. The evaporation is conducted at a temperature from about 150° C. to about 220° C.; another range is from about 180° C. to about 200° C. The combination of evaporators 321 and 350 are operated so as to concentrate the mother liquor 301 as represented by stream 301 to a condition wherein 95-99 wt % of the solvent, typically acetic acid and water, is removed from the mother liquor 301.

In the present process, the condition of the super concentrated mother liquor stream 345 is as a high temperature molten dispersion with only enough remaining solvent to provide pumpability. In one embodiment, a typical composition of the super concentrated mother liquor 345 is shown in Table 1. Generally, the mass composition of the sum total of all compounds shown in Table 1, excluding water and acetic acid, in the super concentrated mother liquor 345 can vary between about 5 wt % to about 80 wt % based on the total weight of the super concentrated mother liquor 345. Another range for the sum total of all compounds shown in Table 1, excluding acetic acid and water, in the super concentrated mother liquor 345 can be all combinations of upper and lower ranges where the lower ranges are 5 wt %, 10 wt %, 15 wt %, 20 wt %, 25 wt %, 30 wt %, 35 wt %, 40 wt % and the upper ranges are 80 wt %, 75 wt %, 70 wt %, 65 wt %, 60 wt %, 55 wt %, 50 wt %, 45 wt % based on the total weight of the super concentrated mother liquor 345. Further, ranges stated in this disclosure and the claims that follow should be understood to disclose the entire range specifically and not just the end point(s). For example, disclosure of the range 0 to 10 should be taken to specifically disclose 2, 2.5, 3.17 and all other number subsumed and not just 0 and 10.

Step (c) comprises mixing in a mixing zone 348 a water-solvent solution 306 with the super concentrated mother liquor stream 345 to form an aqueous mixture 307.

The super concentrated mother liquor steam 345 is then subjected to extraction of the metal catalyst in the mixing zone 348 by introduction of a water-solvent solution 306 which can contain water or a water-acetic acid or a water-solvent solution to form an aqueous mixture in stream 307 wherein at least 80% of the metal catalyst is recovered in the aqueous phase of the aqueous mixture 307. Typically, at least 90% of the metal catalyst is recovered in the aqueous phase of the aqueous mixture 307. The water-solvent solution comprises water and optionally an additional solvent. The solvent can be any substance capable of dissolving the metal catalyst to form a uniformly dispersed solution at the molecular or ionic size level. Typically, the solvent comprises acetic acid, but solvents that have been previously mentioned in step (a) can also be utilized.

The mixing zone 348 comprises a vessel and/or device or a plurality of vessels or devices wherein there is sufficient residence time for the metal catalyst and/or halogen compounds (e.g. bromine) to dissolve into solution. Examples of such vessels are devices include, but are not limited to, a tank and a stirred or agitated tank. In this step, it is not necessary to completely dissolve the mixture. One method is to utilize only the necessary amount of water to obtain the level of the metal catalyst recovery desired. However, the addition of water solvent solution 306 also serves to quench the mixture to a temperatures in the range of about 60° C. to about 95° C., another range is about 80° C. to about 90° C. The quenching is done for about 0.5 to about 4 hours, another range is about 1 to about 2 hours. By this treatment organic bromides are reacted to yield inorganic bromides that are for example, preferentially retained in the aqueous fraction exiting an extractor. The quantity of bromine-containing compounds purged from the system along with the unwanted impurities is thereby minimized. The heat treatment conserves bromides and simplifies disposal of the organic impurities.

The addition of water in the mixing zone 348 not only recovers the metal catalyst in the super concentrated mother liquor, but also aids in pumping the aqueous mixture 307. It is desirable to keep the aqueous mixture 307 circulating with an external circulation loop.

In one embodiment, a typical composition of the aqueous mixture is shown in Table 1. Generally, the mass composition of the aqueous mixture 307 in this embodiment generally can vary wherein the mass ratio of water to acetic acid is in the range of about 1:1 to 99:1 and wherein the sum aggregate of isophthalic acid, benzoic acid, 4-carboxybenzaldehyde, and terephthalic comprises between about 1000 ppm to about 65 wt % of the total weight of the aqueous mixture 307. Another range can be all combinations of upper and lower ranges wherein the sum aggregate of isophthalic acid, benzoic acid, 4-carboxybenzaldehyde, and terephthalic have a lower range of 5 wt %, 10 wt %, 15 wt %, 20 wt %, 25 wt %, 30 wt %, 35 wt %, 40 wt % and a upper range of 65 wt %, 60 wt %, 55 wt %, 50 wt %, 45 wt % based on the total weight of the aqueous mixture 307.

When separating in the solid liquid separation zone 351 is performed, a small amount of extraction solvent in conduit 311, generally about 1 to about 10% by weight, preferably about 5% by weight, may be added to the mixing zone 348 to enhance slurry handling by reducing adherence of solids to the side of, for example, a slurry feed tank. This is represented by the dashed arrow from stream 311 in FIG. 1.

Step (d) comprises optionally separating organic impurities 312 from the aqueous mixture 307 in a solid-liquid separation zone 351 to form a purified aqueous mixture 308.

The aqueous mixture stream 307 can be optionally fed to a solid-liquid separation zone comprising a solid-liquid apparatus, 351, wherein organic impurities 312 may be removed from the aqueous mixture 307 to form a purified aqueous mixture 308 and organic impurities 312. There are no limitations on the type of solid-liquid separation apparatus as long as it is sufficient to remove organic impurities 312 from the aqueous mixture 307. Examples of such apparatuses include, but are not limited to, filters, centrifuges, cyclones, hydroclones, etc.

The organic impurities can comprise numerous compounds typically associated with TPA production. Examples of typical organic impurities include, but are not limited to, isophthalic acid, trimellitic acid, benzoic acid, phthalic acid, fluorenones compounds, p-toluic acid, and 4-carboxybenzaldehyde. In one embodiment, a typical composition of the purified aqueous mixture 308 is shown in Table 1. The mass composition of the purified aqueous mixture 308 in this embodiment comprises acetic acid, water, isophthalic acid, benzoic acid, 4-carboxybenzaldehyde, terephthalic acid, and cobalt; wherein the sum aggregate of the isophthalic acid, benzoic acid, 4-carboxybenzaldehyde, and terephthalic acid comprise between about 1 wt % to 70% based on the total weight of the purified aqueous mixture 308; wherein the sum aggregate of isophthalic acid and terephthalic acid comprise no more than 10 wt % of the purified aqueous mixture 308. Another range can be all combinations of upper and lower ranges wherein the sum aggregate of isophthalic acid, benzoic acid, 4-carboxybenzaldehyde, and terephthalic have a lower range of 5 wt %, 10 wt %, 15 wt %, 20 wt %, 25 wt %, 30 wt %, 35 wt %, 40 wt % based on the total weight of the purified aqueous mixture 308 and a upper range of 65 wt %, 60 wt %, 55 wt %, 50 wt %, 45 wt % based on the total weight of the purified aqueous mixture 308; and wherein the sum aggregate of isophthalic acid and terephthalic acid comprise no more than 10 wt % based on the total weight of the purified aqueous mixture 308.

As previously stated when the solid-liquid separation zone 351 is utilized, a small amount of extraction solvent in conduit 311, generally about 1 to about 10% by weight, preferably about 5% by weight may be added to the mixing zone 348 to enhance slurry handling by reducing adherence of solids to the side of, for example, a slurry feed tank. This is represented by the dashed arrow from stream 311 in FIG. 1.

Step (e) comprises adding an extraction solvent 311 to the aqueous mixture 307 or the purified aqueous mixture 308 in an extraction zone 323 to form an extract stream 309 and the raffinate stream 310.

The aqueous mixture 307 or the purified aqueous mixture 308 is fed to an extraction zone 323 wherein the aqueous mixture 307 or the purified aqueous mixture 308 and the extraction solvent 311 are contacted in the extraction zone 323. The aqueous mixture 307 or the purified aqueous mixture 308 and the extraction solvent 311 are mixed to form an extract stream 309 comprising solvent, water organic impurities, and organic solvent which forms a lighter phase, and the raffinate stream 310 comprising a metal catalyst, corrosion metals, and water. The extract stream 309 is withdrawn as an overhead stream, and the raffinate stream 310 is withdrawn from the bottom of extractor in the extraction zone 323. In this invention, one embodiment of the extraction zone 323 is a single stage extractor. In an embodiment of the invention, the extraction zone comprises a counter current extractor.

The extraction solvent 311 used in the extractor should be substantially water-insoluble to minimize the amount of organic solvent dissolved in the aqueous fraction. Additionally, the extraction solvent 311 is preferably an azeotropic agent which serves to assist solvent recovery from the organic extract. Solvents, which have proven to be particularly useful are C1 to C6 alkyl acetates, particularly n-propyl acetate (n-PA), isopropyl acetate, isobutyl acetate, sec-butyl acetate, ethyl acetate and n-butyl acetate, although other water-insoluble organic solvents having an appropriate density and a sufficiently low boiling point may also be used, such as p-xylene. N-propyl acetate and isopropyl acetate are particularly preferred due to their relatively low water solubility, excellent azeotropic behavior, and their ability to remove the remaining acetic acid as well as high-boiling organic impurities from the aqueous mixture.

The extraction can be effected using extraction solvent ratios from about 1 to about 4 parts by weight extraction solvent per part of extractor feed depending on the extractor feed composition. Space velocities of the combined feeds to the extractor generally range from about 1 to about 3 $hr^{-1}$. Although the extraction can be conducted at ambient temperature and pressure, heating the extraction solvent 311 and extractor to about 30°-70° C. Another range of about 40° C. to about 60° C. can be used. Although the extract stream 309 comprises small amounts of the metal catalyst and corrosion metals, essentially all of the metal catalyst and the majority of the remaining corrosion metals are contained in the heavier phase, the raffinate stream 310.

Step (f) comprises optionally separating the extract stream 309 and the solvent rich stream 344 in a separation zone 324 to form a high boiling point organic impurities stream 315 and a recovered extraction solvent stream 317.

The extract stream 309 comprises organic solvent and organic impurities. The extract stream 309 can further comprises acetic acid and water, often in minor amounts. The extract stream 309 may be distilled in a separation zone comprising conventional distillation equipment. The distillation equipment is operated at process conditions sufficient to recover a majority of the extraction solvent, typically n-propyl acetate, from the extract stream 309 into the recovered extraction solvent stream 317. Convention distillation equipment includes, for example, a distillation column. One key feature to this invention is the re-introduction of the solvent rich stream 344 into the separation zone 324.

Most of the organic impurities are extracted by the organic solvent in the extraction zone 323. This occurs because the organic impurities show a high degree of solubility for the organic solvent and to a lesser extent for acetic acid. By distilling the lighter phase from the extractor, the organic solvent is evaporated allowing the organic impurities to concentrate in the column underflow. This results in a high probability for plugging and precipitation of solids. By utilizing the solvent rich stream 344, the organic impurities in the column underflow can be effectively diluted and thereby solubilized by acetic acid in the column underflow. In an embodiment of the invention, the solvent rich stream 344 comprises a solvent selected from the group consisting of n-propyl acetate, isopropyl acetate, isobutyl acetate, sec-butyl acetate, ethyl acetate and n-butyl acetate.

The use of the solvent rich stream 344, from the previous evaporation serves two functions. First, the loss of the organic solvent is minimized since the solvent rich stream 344 effectively displaces the organic solvent in the column underflow. Second, the use of acetic-acid rich vapor provides significant enthalpy needed for driving the distillation/separation process.

The separation zone 324 will need to process significantly less hydraulic load than a typical purge process due to the greater concentration of mother liquor. Recovered extraction solvent and acetic acid may be recycled to the extractor and oxidative reactor, respectively. The high-boiling organic impurities are removed as sludge from the base of the distillation column for disposal.

Although the composition of the various streams in the process varies depending on the process conditions, a typical composition of the streams are shown in Table 1. In Table 1, the components are shown in the left hand column and the amount of these components in each stream in the FIG. 1 are shown in the number column corresponding to the number of the stream in FIG. 1. The amounts of the components shown in Table 1 can be any measurement of weight as long as it is consistent for all components and all streams. For example, the mother liquor 301 has acetic acid in the amount of 915 pounds, 915 grams, etc.

We claim:
1. A process comprising:
   (a) evaporating a mother liquor comprising a carboxylic acid, a metal catalyst, impurities, water and a solvent in a first evaporator zone to produce a vapor stream and a concentrated mother liquor stream;
   (b) evaporating said concentrated mother liquor stream in a second evaporator zone to form a solvent rich stream and a super concentrated mother liquor stream; wherein said super concentrated mother liquor stream is a high temperature molten dispersion; wherein said evaporating in said second evaporator zone is conducted at a temperature from about 150° C. to about 220° C.;
   (c) mixing in a mixing zone a water-solvent solution and optionally an extraction solvent with said super concentrated mother liquor stream to form an aqueous mixture;
   (d) adding an extraction solvent to said aqueous mixture in an extraction zone to form an extract stream and a raffinate stream; and
   (e) separating said extract stream and said solvent rich stream in a separation zone to form a high boiling point organic impurities stream and a recovered extraction solvent stream.

2. The process according to claim 1 wherein about 50 wt % to about 80 wt % of said solvent is removed from said mother liquor in step (a).

3. The process according to claim 1 wherein about 95 wt % to about 99 wt % of said solvent and water is removed from said mother liquor in step (a) and step (b) combined.

4. The process according to claim 1 wherein said extraction solvent is optionally added in step (c) in an amount of about 1 to about 10 percent by weight.

5. The process according to claim 1 wherein said water-solvent solution is added to quench said aqueous mixture to a temperature range of about 60° C. to about 95° C.

6. A process according to claim 1 wherein said extraction zone comprises a counter current extractor.

TABLE 1

Material Balance
Process Material Balance
Stream in FIG. 1

| | 301 | 304 | 305 | 344 | 345 | 306 | 307 | 308 | 309 | 310 | 311 | 312 |
|---|---|---|---|---|---|---|---|---|---|---|---|---|
| Acetic Acid | 915.0 | 534.1 | 380.9 | 335.2 | 45.8 | — | 45.8 | 45.3 | 44.1 | 1.2 | — | 0.4 |
| Water | 55.0 | 39.3 | 15.7 | 14.7 | 1.0 | 80.0 | 81.0 | 80.2 | 35.6 | 44.5 | — | 0.7 |
| n-Propyl Acetate | — | — | — | — | — | — | — | — | 399.0 | 1.0 | 400.0 | — |
| Terephthalic Acid | 0.71 | — | 0.71 | — | 0.71 | — | 0.71 | 0.70 | 0.70 | — | — | — |
| Isophthalic Acid | 5.83 | — | 5.83 | — | 5.83 | — | 5.83 | 5.78 | 5.71 | 0.07 | — | 0.05 |
| Phthalic Acid | 3.81 | — | 3.81 | 0.12 | 3.69 | — | 3.69 | 3.66 | 3.36 | 0.29 | — | 0.03 |
| Benzoic Acid | 8.12 | 0.06 | 8.06 | 2.27 | 5.79 | — | 5.79 | 5.73 | 5.73 | — | — | 0.05 |
| 4-Carboxybenzaldehyde | 1.56 | — | 1.56 | — | 1.56 | — | 1.56 | 1.54 | 1.52 | 0.02 | — | 0.01 |
| Trimellitic Acid | 1.17 | — | 1.17 | — | 1.17 | — | 1.17 | 1.16 | 1.01 | 0.14 | — | 0.01 |
| Paratoluic Acid | 2.96 | 0.01 | 2.95 | 0.50 | 2.44 | — | 2.44 | 2.42 | 2.39 | 0.03 | — | 0.02 |
| Paratolualdehyde | 0.51 | 0.05 | 0.46 | 0.26 | 0.20 | — | 0.20 | 0.20 | 0.20 | — | — | — |
| Others | 2.50 | — | 2.50 | — | 2.50 | — | 2.50 | 2.38 | 2.14 | 0.24 | — | 0.13 |
| Organic Bromide | 1.30 | — | 1.30 | — | 1.30 | — | 0.90 | 0.86 | — | 0.85 | — | 0.05 |
| Ionic Bromide | 0.34 | — | 0.34 | — | 0.34 | — | 0.74 | 0.70 | — | 0.70 | — | 0.04 |
| Cobalt | 1.44 | — | 1.44 | — | 1.44 | — | 1.44 | 1.37 | 0.01 | 1.35 | — | 0.07 |
| Manganese | 0.10 | — | 0.10 | — | 0.10 | — | 0.10 | 0.10 | — | 0.09 | — | — |
| Corrosion Metals | 0.08 | — | 0.08 | — | 0.08 | — | 0.08 | 0.08 | — | 0.08 | — | — |
| Total | 1000 | 573 | 427 | 353 | 74 | 80 | 154 | 152 | 502 | 51 | 400 | 2 |

*The amounts of the components shown in Table 1 can be any measurement of weight as long as it is consistent for all components and all streams 7. A process according to claim 1 wherein said extraction zone comprises a single stage extractor.

8. A process according to claim 1 wherein said solvent rich stream comprises a solvent selected from the group consisting of n-propyl acetate, isopropyl acetate, isobutyl acetate, sec-butyl acetate, ethyl acetate and n-butyl acetate.

9. A process according to claim 1 wherein said second evaporator zone comprises an evaporator operated at a temperature of about 150° C. to about 200° C.

10. A process according to claim 1 where said first evaporator zone is operated at a pressure of greater that 14.6 psia.

11. A process comprising:
(a) evaporating a mother liquor comprising a carboxylic acid, a metal catalyst, impurities, water and a solvent in a first evaporator zone to produce a vapor stream and a concentrated mother liquor stream;
(b) evaporating said concentrated mother liquor stream in a second evaporator zone to form a solvent rich stream and a super concentrated mother liquor stream; wherein said super concentrated mother liquor stream is a high temperature molten dispersion; wherein said evaporating in said second evaporator zone is conducted at a temperature from about 150° C. to about 220° C.;
(c) mixing in a mixing zone a water-solvent solution with said super concentrated mother liquor stream to form an aqueous mixture;
(d) separating organic impurities from said aqueous mixture in a solid-liquid separation zone to form a purified aqueous mixture;
(e) adding an extraction solvent to said aqueous mixture or said purified aqueous mixture in an extraction zone to form an extract stream and a raffinate stream; and
(f) separating said extract stream and said solvent rich stream in a separation zone to form a high boiling point organic impurities stream and a recovered extraction solvent stream.

12. The process according to claim 11 wherein about 50 wt % to about 80 wt % of said solvent is removed from said mother liquor in step (a).

13. The process according to claim 11 wherein said water-solvent solution is added to quench said aqueous mixture to a temperature range of about 60° C. to about 95° C.

14. The process according to claim 11 wherein said water-solvent solution is added to quench said aqueous mixture to a temperature range of 80° C. to about 90° C.

15. The process according to claim 11 wherein said extraction zone comprises a counter current extractor.

16. The process according to claim 11 wherein said extraction zone comprises a single stage extractor.

17. The process according to claim 11 wherein said solvent rich stream comprises a solvent selected from the group consisting of n-propyl acetate, isopropyl acetate, isobutyl acetate, sec-butyl acetate, ethyl acetate and n-butyl acetate.

* * * * *